(12) United States Patent
Janigro et al.

(10) Patent No.: US 6,667,172 B2
(45) Date of Patent: Dec. 23, 2003

(54) CELL AND TISSUE CULTURE MODELING DEVICE AND APPARATUS AND METHOD OF USING SAME

(75) Inventors: Damir Janigro, Cleveland Heights, OH (US); Mark S. McAllister, Rocky River, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 09/957,063

(22) Filed: Sep. 19, 2001

(65) Prior Publication Data

US 2003/0054545 A1 Mar. 20, 2003

(51) Int. Cl.$^7$ .............................. C12M 1/34; C12M 3/06
(52) U.S. Cl. ....................... 435/297.4; 435/29; 435/400; 435/288.2; 435/359; 359/398; 210/321.8
(58) Field of Search .......................... 435/29, 32, 325, 435/366, 368, 398–400, 288.2, 297.2, 297.4; 210/321.8; 472/48; 359/398

(56) References Cited

U.S. PATENT DOCUMENTS

| | | | |
|---|---|---|---|
| 3,821,087 A | | 6/1974 | Knazek et al. |
| 3,883,393 A | | 5/1975 | Knazek et al. |
| 3,976,576 A | * | 8/1976 | Jacobsen et al. ......... 210/321.8 |

(List continued on next page.)

FOREIGN PATENT DOCUMENTS

| | | | | |
|---|---|---|---|---|
| EP | 942066 A2 | * | 9/1999 | ........... C12N/05/06 |
| WO | WO 200164849 A1 | * | 9/2001 | ........... C12N/05/02 |

OTHER PUBLICATIONS

Stanness et al.'A Dynamic Model of the Blood–Brain Barrier "In Vitro". NeuroToxicology. vol. 17 (1996), No. 2, pp. 481–496.*

Morphological and Functional Characterization of an In Vitro Blood–Brain Barrier Model; Brain Research 771; 329–342 (1997).

An In Vitro Blood–Brain Barrier Model: Cocultures Between Endothelial Cells and Organotypic Brain Slice Cultures; The National Academy of Sciences; vol. 95, pp. 1840–1845; Feb. 1998.

Mechanisms of Glucose Transport at the Blood–Brain Barrier: an In Vitro Study; McAllister, Mark S. et al.; (E–Mail: janigrd@ccf.org for more information). (No Date Provided).

Understanding the Physiology of the Blood–Brain Barrier: In Vitro Models; Grant, Greald et al.; News Physiol. Science, vol. 13; Dec. 1998.

Dynamic In Vitro Modeling of the Blood–Brain Barrier: A Novel Tool for Studies of Drug Delivery to the Brain; Janigro, Damir et al.; Elsevier Science, vol. 2, No. 1; Jan. 1999.

A New Model of the Blood–Brain Barrier: Coculture of Neuronal, Endothelial and Glial Cells Under Dynamic Conditions; Stanness, Kathe et al.; Neuropharmacology and Neurotoxicology; vol. 10 No. 18, 3725–3731; Dec. 16, 1999.

*Primary Examiner*—William H. Beisner
(74) *Attorney, Agent, or Firm*—Raymond A. Miller; Pepper Hamilton LLP

(57) ABSTRACT

A cell and tissue culture modeling device comprising a housing having an interior chamber, an inlet port in fluid communication with the internal chamber, an outlet port in fluid communication with the internal chamber, a plurality of hollow fibers disposed within the interior chamber and traversing the length of the housing between the inlet port and the outlet port. Each of the plurality of hollow fibers has an interior defining an intracapillary space and the interior chamber defines an extracapillary space unoccupied by the plurality of hollow fibers. To access the extracapillary space of the device, a portion of the housing is removable. The device can be used to conduct permeability, drug efficacy, and gene expression studies.

33 Claims, 10 Drawing Sheets

U.S. PATENT DOCUMENTS

| | | |
|---|---|---|
| 4,184,922 A | 1/1980 | Knazek et al. |
| 4,200,689 A | 4/1980 | Knazek et al. |
| 4,201,845 A * | 5/1980 | Feder et al. ............ 435/297.2 |
| 4,206,015 A | 6/1980 | Knazek et al. |
| 4,220,725 A | 9/1980 | Knazek et al. |
| 4,391,912 A | 7/1983 | Yoshida et al. |
| 4,804,628 A | 2/1989 | Cracauer et al. |
| 5,260,210 A * | 11/1993 | Rubin et al. ............... 435/325 |
| 5,282,966 A * | 2/1994 | Walker .................. 210/321.8 |
| 5,627,070 A | 5/1997 | Gruenberg |
| 5,759,846 A | 6/1998 | Stoppini et al. |
| 5,958,762 A | 9/1999 | Stoppini et al. |
| 6,001,585 A | 12/1999 | Gramer |
| 6,022,733 A * | 2/2000 | Tam et al. ............... 435/287.1 |
| 6,130,056 A | 10/2000 | Correges |

* cited by examiner

CELL AND TISSUE CULTURE MODELING DEVICE AND APPARATUS AND METHOD OF USING SAME

BACKGROUND OF THE INVENTION

Knowledge of the blood-brain barrier (BBB) has progressed rapidly over the past several years as new techniques (e.g. in vitro cell cultures) have become available. Improved technologies for the monitoring of barrier integrity in terms of electrical resistance and macromolecule permeability are readily accessible. Concomitant with the advancement of these techniques has come a wealth of knowledge regarding the relevant factors that promote the expression of a BBB phenotype particularly in endothelial cells.

The BBB maintains the homeostasis of the brain microenvironment, which is crucial for neuronal activity and function. Brain microvascular endothelial cells (EC) that constitute the BBB are responsible for the transport of metabolites, precursors and nutrients from the blood to the brain. The same cells are involved in the clearance of potassium and hydrogen ions from the brain. While blood-brain barrier EC retard the transcellular migration of most hydrophilic solutes, nutrients and sugars gain rapid access into the brain. In mammals and in higher vertebrates, the sites of the BBB are the complex tight junctions between EC that prevent the paracellular migration of hydrophilic molecules from blood to brain and vice versa. The perivascular glia process with encompass the basal lamina of the endothelial cells in the central nervous system influence the integrity of the tight junctions. Specialized transporters for sugars (e.g. glucose) and amino acids have been described in blood-brain barrier EC and account for the transendothelial permeability of otherwise membrane-impermeant substances.

As one may expect given the seemingly opposite properties of these BBB cells, two different subcellular mechanisms are responsible for the 'barrier' and 'transport' features of blood-brain barrier EC: tight junctions and specialized transcellular transporters, including micropinocytotic vesicles for macromolecules.

An often neglected aspect of the BBB relates to its capacity to act simultaneously as a barrier and as a transporter for any ion or molecule. For example, the BBB is virtually impermeant to intraluminal potassium ($K_{plasma}$). However, brain (i.e. abluminal) potassium is transported to the blood by a specialized and topographically segregated Na/K-ATPase. Thus, by combining the tight junction-mediated 'tightness' of the BBB with an asymmetric transporter, $K_{CSF}$ remains constant in spite of $K_{plasma}$ variations or parenchymal increases resulting from neuronal activity.

Most of these specialized properties (tight junctions, micropinocytotic vesicles, transporters, ion homeostasis mechanisms) are bestowed on endothelial cells by the brain tissue. Peripheral capillaries that vascularize brain tissue acquire BBB properties. However, isolated blood-brain barrier EC lose their properties after culturing in vitro.

Therefore, two key factors must be present in order for central nervous system endothelial cells to express a barrier phenotype in vitro which distinguishes them from their peripheral counterparts. First, the exposure of the apical membrane to shear stress, which is generated by the flow of blood across the apical surfaces of the endothelial cells, is vital to promote growth inhibition and differentiation of endothelial cells. Also, the exposure to shear stress serves to induce metabolic changes that limit the oxygen and substrate consumption of such cells and allow for trafficking of metabolic fuels to the brain. A by-product of the metabolic changes induced by flow is an improved capacity for endothelial cells to handle oxidative stress. The second vital factor for BBB formation by endothelial cells is exposure of these cells to as yet unidentified "permissive" or "promoting" factors presumably secreted by glia, specifically astrocytes. The basis for this comes from several series of experiments documenting close apposition of astrocyte foot processes to endothelial cells in instances of barrier expression and the absence of such expression when astrocytes or astrocytic factors are lacking. Astrocytic influences promote both a variety of changes in gene expression in endothelial cells as well as phenotypic changes including segregation of transporters and enzymes.

The goal of any study of BBB physiology or biology is to reproduce as many aspects as possible of the in vivo endothelial cells. The apposition of endothelial cell and astrocyte cell cultures in physically separate, but biochemically contiguous compartments and the exposure of the endothelial cells to apical shear stress are primary features of any dynamic model of the blood-brain barrier. Furthermore, an in vitro BBB model should simulate as many of the following properties as possible: (1) expression of tight junctions between ECs and the relative lack of pinocytotic vesicles (commonly assessed by measuring trans-endothelial electrical resistance (TEER) or permeability to radioactive molecules of poor or negligible permeation such as sucrose or mannitol); (2) selective (and asymmetric) permeability to physiologically relevant ions, such as $Na^+$ or $K^+$; (3) selective permeability to molecules, based on their molecular weight and oil/water partition coefficient; (4) expression of BBB-specific transporters for metabolic substrates or building blocks necessary for neuronal and glial cell physiology; and (5) functional expression of mechanisms of active extrusion of otherwise permeable substances (such as antineoplastic agents).

A first attempt at an in vitro BBB model included the use of cone and plate viscometers as well as parallel plate apparatuses combined with semipermeable membranes that are able to generate shear stress and co-culture conditions. However, these models did not possess the three-dimensional architecture characteristic of brain tissue in situ and lacked the necessary glial factors. Another model design known in the art uses a hollow fiber apparatus to conduct BBB studies. This model results from a modification of a traditional cell culture system that is normally used for extensive culturing of non-EC cells. The general design of the hollow fiber apparatus is derived from attempts to develop a 'cell factory'. U.S. Pat. No. 3,821,087 to Knazek et al. and U.S. Pat. No. 4,220,725 to Knazek et al. describe cell culturing devices using hollow fibers. Since then, these cell culturing devices have been extensively exploited for mass production of rare cell types, antibody production, and modeling of organ-like structures such as the BBB. Ott et al. used a hollow fiber cell culture apparatus for studies of flow-mediated effects on endothelial cell growth. A cell culturing device that is commercially available is CELL-MAX® from Spectrum Laboratories.

Applicant has co-authored several publications describing attempts to simulate the blood brain barrier utilizing cell culture models by co-culturing endothelial cells intraluminally (i.e., intracapillary) and glia extraluminally (i.e., extracapillary). These publications include "A New Model of the Blood Brain Barrier: Co-Culture of Neuronal, Endothelial, and Glial Cells Under Dynamic Conditions,"

NeuroReport, Vol. 10, No. 1816, December 1999; "Understanding the Physiology of the Blood Brain Barrier: In Vitro Models," News in Physiological Sciences, Volume 13, December 1998; "Dynamic In Vitro Modeling of the Blood Brain Barrier: A Novel Tool for Studies of Drug Delivery to the Brain," PSTT, Vol. 2, No. 1, January 1999; Morphological and Functional Characterization of an In Vitro Blood-Brain Barrier Model," Brain Research, No. 771, 1997; and Mechanisms of Glucose Transport at the BBB: An In Vitro Study, Brain Research 409, 2001 which are all hereby incorporated by reference in their entireties to the extent they discuss the utilization of cell culturing models to simulate the BBB.

However, although cell culture models may be used to model the BBB, the cell culture models known in the art have proven to be of limited applicability. For example, these models provide poor visualization of the intracapillary or extracapillary space to assess morphologic and/or phenotypic changes in the cells of interest, and do not appropriately provide the necessary access for the introduction of outside agents or samples. The volume of and physical access to the extracapillary space in these cell culture models known in the art allow for only cell suspension introduction. Finally, the cell inoculation volume and media requirements of these models are relatively large in light of the fact that these models are not reusable.

It is desirable to develop a cell and tissue culture modeling device and apparatus that addresses these limitations, but also adds functionality, modularity, and expandability to the experimental repertoire unavailable under the current configuration.

SUMMARY OF THE INVENTION

Generally, the present invention is directed to a cell and tissue culture modeling device and apparatus and method of using the same.

In one embodiment of the present invention, the cell and tissue culture modeling device includes a design amenable to light and fluorescence microscopy. For instance, the thickness of the device is within the resolution range of light and fluorescence microscopes, thus examination of the extracapillary space is achievable. The capacity to remove a single or multiple hollow fibers during the course of an experiment addresses the issue of visualization of the endothelial cell provides an advantage to the present invention. Also, the relative flatness of the device makes it modular and thus automation of simultaneous permeability determinations of compounds and multiplexing is possible.

In a preferred embodiment of the present invention, the device includes housing wherein at least a portion of the housing is removable to access the extracapillary space. This access to the extracapillary space provides for the introduction of tissue samples, neurochips, or other testing devices into the extracapillary space.

In a preferred embodiment of the present invention, the relative size of the extracapillary space to the intracapillary space is increased to accommodate the tissue samples in addition to cell suspensions. Adequate permeability measurements are still obtainable given the increase in the size of the extracapillary compartment. Also, additional access is provided to the extracapillary space through the use of access ports that have the ability to measure transendothelial electrical resistance.

In yet another alternative embodiment of the present invention, each component of the device is downsized to varying degrees such that the amount of cells required to initiate an experiment has been substantially reduced (by nearly four times) and the media volume required to perfuse the system and maintain cell viability (approximately half). When considering the use of expensive growth factors or the need to dispose of radiolabeled macromolecules, total media requirements can be an important issue.

Cell and tissue culture modeling devices have a variety of applications ranging from the in vitro modeling of the blood-brain barrier for focused individual study to fully automated microdialysis-driven permeability determinations for multiple biologically active molecules on a mass scale. Other relevant applications of the present invention include a clinically predictive tool for the efficacy of chemotherapeutic agents in the treatment of primary central nervous system malignancy, the incorporation of a brain slice to the system to simultaneously evaluate drug penetration and efficacy, as well as time course driven monitoring of gene expression profiles of endothelial cells and brain parenchymal cells under conditions which promote cell maturation and differentiation.

According to the present invention, a cell and tissue culture modeling device (hereinafter referred to as "device") comprises a housing having an interior chamber and an inlet port and an outlet port. Both the inlet and outlet ports are in fluid communication with the internal chamber. The device also includes a plurality of hollow fibers disposed within the interior chamber. The hollow fibers traverse the length of the housing between the inlet port and the outlet port. Each of the hollow fibers has an interior defined as an intracapillary space. The inlet port permits fluid to enter the housing, via the intracapillary space of each hollow fiber, and exit the housing through the outlet port. The hollow fibers occupy only a portion of the internal chamber. The unoccupied portion of the internal chamber is defined as an extracapillary space. A portion of the housing is removable to access the extracapillary space.

The housing includes a pair of opposing end walls and a pair of opposing side walls. In at least one of the pair of opposing side walls, at least one access port is provided in fluid communication with the extracapillary space. In one of the end walls of the housing, the inlet port is provided. In the other end wall of the housing, the outlet port is provided. The housing also includes a top wall wherein at least a section of said top wall defines a top panel. The top panel is the portion of the housing that is removable to access the extracapillary space and is removably attached to the housing. The device may also include a gasket installed in between the top panel and the housing to create a watertight extracapillary space. The housing also includes a bottom wall wherein at least a portion of the bottom wall defines a bottom panel made of laboratory quality glass.

Each of the plurality of hollow fibers has a wall that includes a plurality of pores that provide fluid communication between the intracapillary space and the extracapillary space. The size of each of the plurality of pores is between about 0.01 $\mu$m and about 0.50 $\mu$m. The hollow fibers are formed of a material selected from the group consisting of polypropylene, polyester, polystyrene, polycarbonate, nitrocellulose compound, polyethylene, polysolfone, cellulose, polymethyl methacrylate, polyacrylonitrile, and polyvinylidene fluoride. The device of claim 6, wherein said plurality of hollow fibers are suspended and fixed in said inlet port and outlet port using an epoxy adhesive to create a watertight extracapillary space.

In another embodiment, the present invention provides a dynamic three-dimensional cell and tissue culture modeling apparatus (hereinafter referred to as "apparatus"). The apparatus comprises at least one cell and tissue culture modeling device according to the present invention, a pump system, a media reservoir, and a first, second, and third conduit. The first conduit interconnects the media reservoir to the pump system, while the second conduit interconnects the pump system to the inlet port of each device, and the third conduit interconnects the outlet port of each device to the media reservoir. The second conduit is in fluid communication with the intracapillary spaces of the plurality of hollow fibers in the inlet port. The third conduit is in fluid communication with the intracapillary spaces of the plurality of hollow fibers in the outlet port. Preferably, the pump system is a variable speed pump system that generates pulsatile flow. Preferably, the first, second, and third conduit is gas permeable tubing. The apparatus may further comprise a first valve positioned between the pump system and the media reservoir and a second valve positioned between the pump system and each device to ensure unidirectional flow.

In another embodiment, at least one intracapillary space of the plurality of hollow fibers is inoculated with a first cell suspension. Preferably, the first cell suspension includes endothelial cells.

In yet another embodiment, the extracapillary space is inoculated with a second cell suspension. Preferably, the second cell suspension includes glial cells such as astrocytes.

Also, the present invention provides for a method of determining the permeability of an agent across a capillary wall comprising the steps of providing a cell culture model having a plurality of capillaries disposed within an interior chamber which defines an extracapillary space unoccupied by the plurality of capillaries, each of the plurality of capillaries including a plurality of pores that provide fluid communication between an intracapillary space and the extracapillary space; passing an agent having a known concentration through the plurality of intracapillary spaces; sampling the extracapillary space to provide an extracapillary space sample; and analyzing the extracapillary space sample to determine the permeability of the agent across each of the capillary walls. The plurality of intracapillary spaces may be inoculated with endothelial cells and the extracapillary space may be inoculated with glial cells such as astrocytes. A microdialysis-driven sample probe can accomplish the sampling step. A second cell culture model may be introduced to allow for the simultaneous determination of permeability values of at least two agents in a single experiment.

Furthermore, the present invention provides for a method of determining the efficacy of a drug comprising the steps of providing a model that exhibits the properties of a functional blood brain barrier, the model having a plurality of intracapillary spaces and an extracapillary space accessible by an access panel; placing a tissue sample into the extracapillary space; passing an agent through the plurality of intracapillary spaces; and analyzing the tissue sample for responsiveness to the agent. The tissue sample may be a cancerous tissue sample or a brain tissue sample. The agent that passes through the plurality of intracapillary spaces may be a chemotherapeutic agent. The method may further comprise the step of placing a neurochip in the extracapillary space before placing the brain tissue sample into the extracapillary space, wherein the brain tissue sample is placed onto the surface of the neurochip. The neurochip is capable of studying the electrophysiological activity of the brain tissue sample. In this scenario, the brain tissue sample may be an epileptic brain tissue sample and the agent may be an anticonvulsant agent. Finally, the method may further comprise the step of examining the tissue sample in the extracapillary space with a microscope.

Additionally, the present invention provides for a method of determining gene expression over time in cells comprising the steps of providing a cell culture model having a plurality of hollow fibers disposed within an interior chamber which defines an extracapillary space unoccupied by the plurality of hollow fibers, each of the plurality of hollow fibers includes an intracapillary space inoculated by a cell suspension; passing an agent through the plurality of intracapillary spaces; sampling at least one of the plurality of intracapillary spaces by removing at least one of the plurality of hollow fibers over time; removing the cellular material from at least one of the plurality of hollow fibers; and analyzing the gene expression of the cellular material. The cellular material may include RNA, DNA, metabolites, or protein.

BRIEF DESCRIPTION OF THE DRAWINGS

These and other features, aspects, and advantages of the present invention will become better understood with regard to the following description, appended claims, and accompanying drawings where:

DETAILED DESCRIPTION OF THE INVENTION

Figure 1:
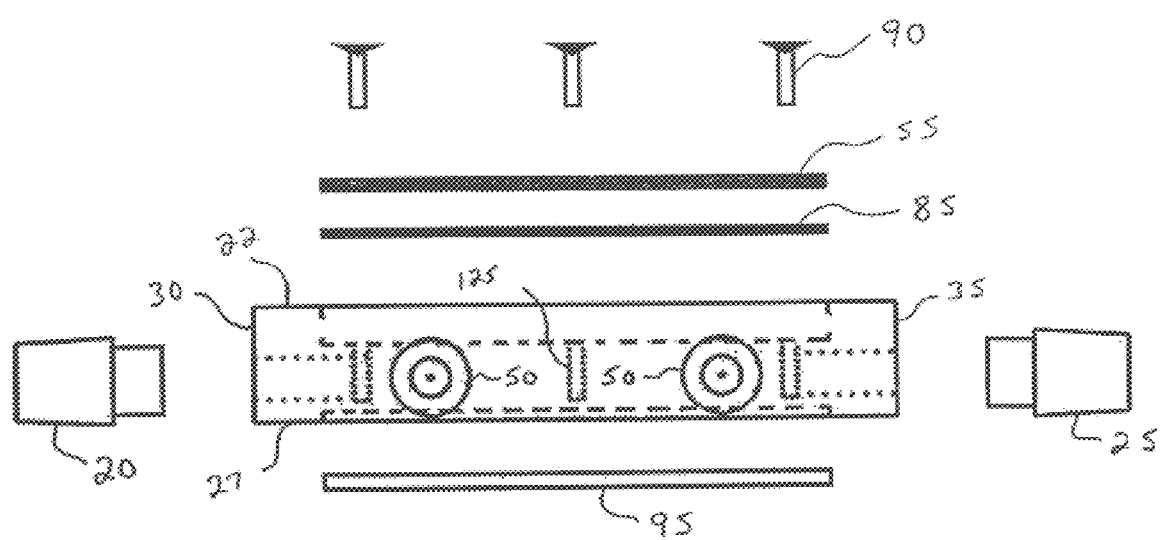
FIG. 1 is a side exploded view of a cell and tissue culture modeling device 10 according to the present invention.
Figure 2:
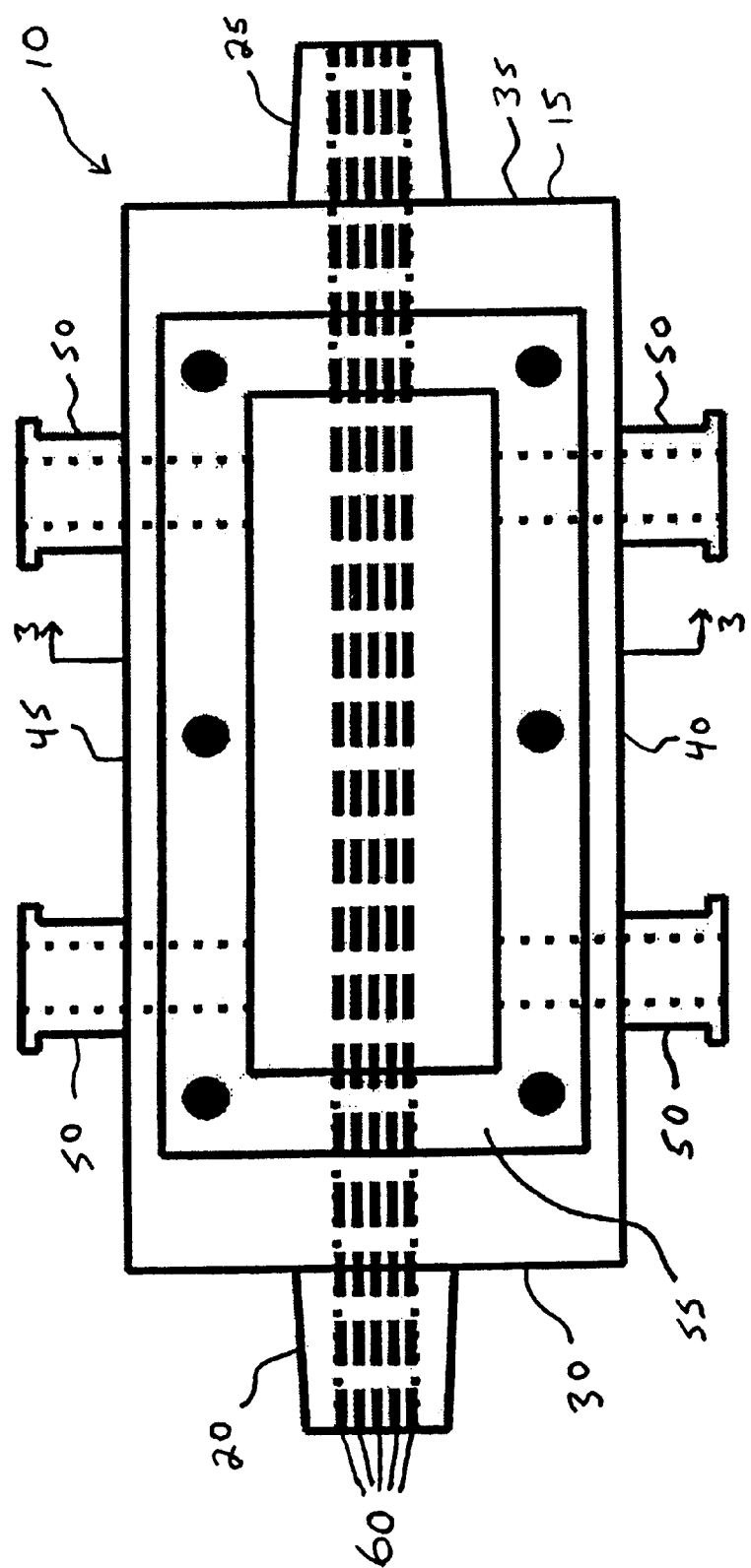
FIG. 2 is a top view of a cell and tissue culture modeling device 10 according to the present invention.

Referring now to the drawings where the illustrations are for the purpose of describing the preferred embodiment of the present invention and are not intended to limit the invention described herein, FIG. 1 is a side exploded view and FIG. 2 is a top view of a dynamic three-dimensional cell and tissue culturing modeling device (hereinafter referred to as "device") 10 according to the present invention. The device 10 comprises a housing 15 having an internal chamber 57. Although the housing 15 depicted in FIGS. 1 and 2 is rectangular shaped, one skilled in the art would recognize that any housing, of suitable shape or dimensions, would be sufficient. Such shapes include cylindrical, spherical, trapezoidal, etc. FIG. 1 depicts the rectangular housing 15 enclosed by a bottom panel 95 and a removable top panel 55. The housing 15 also includes a first end wall 30 and an opposing second end wall 35. FIG. 2 shows the housing 15 having a first side wall 40 and an opposing second side wall 45. The interior chamber 57 is defined between the permanent bottom panel 95, the removable top panel 55, the first and second end walls 30, 35, and the first and second side walls 40, 45. The housing 15 can be manufactured using standard machining techniques or can be specifically injection molded to desired dimensions, in which case the molding process can be used to incorporate the inlet port 20, the outlet port 25, and/or the access ports 50. Preferably, the housing 15 is made of polycarbonate; however, any suitable material will be sufficient. It is preferable that the material is capable of being sterilized (e.g., exposure to ethylene oxide). Injection molding with a sturdier plastic would allow for autoclaving of the housing 15 between experiments.

In the first end wall 30, a hole is milled to precisely accommodate a matching inlet port 20 fitting to such extent that the junction is watertight without the need of adhesive or solvent. In the second end wall 35, another hole of similar size is milled to precisely accommodate a matching outlet port 25 fitting to such extent that the junction is watertight without the need of adhesive or solvent. Although the inlet port 20 fitting and outlet port 25 fitting are both installed in the housing 15 using a press-fit connection, other ways to attach the inlet port 20 and outlet port 25 fittings include threaded attachment, slip-fit with adhesive, or molding them as an integral part of the housing 15. The inlet port 20 and outlet port 25 can accept any size tubing; however, it is preferred that they fit standard 5/16" tubing. In both the first side wall 40 and the second side wall 45, two 5/16" male leur fittings are provided as access ports 50 to the extracapillary space 67. The quantity of access ports 50 can be limited to as few as one and can include more than four depending on the physical limitations of the housing 15. Although the access ports 50 are installed in the housing 15 using a threaded attachment, other ways to attach the access ports 50 include press-fit connection, slip-fit with adhesive, or molding them as an integral part of the housing 15. The access ports 50 allow for multiple and simultaneous sampling, monitoring, or measurement devices. These include sampling needles and microdialysis catheters, electrodes for the measurement of transendothelial electrical resistance, and small-bore multidimensional sensors that can monitor pH, $pO_2$, $pCO_2$, and temperature, etc.

Figure 3:
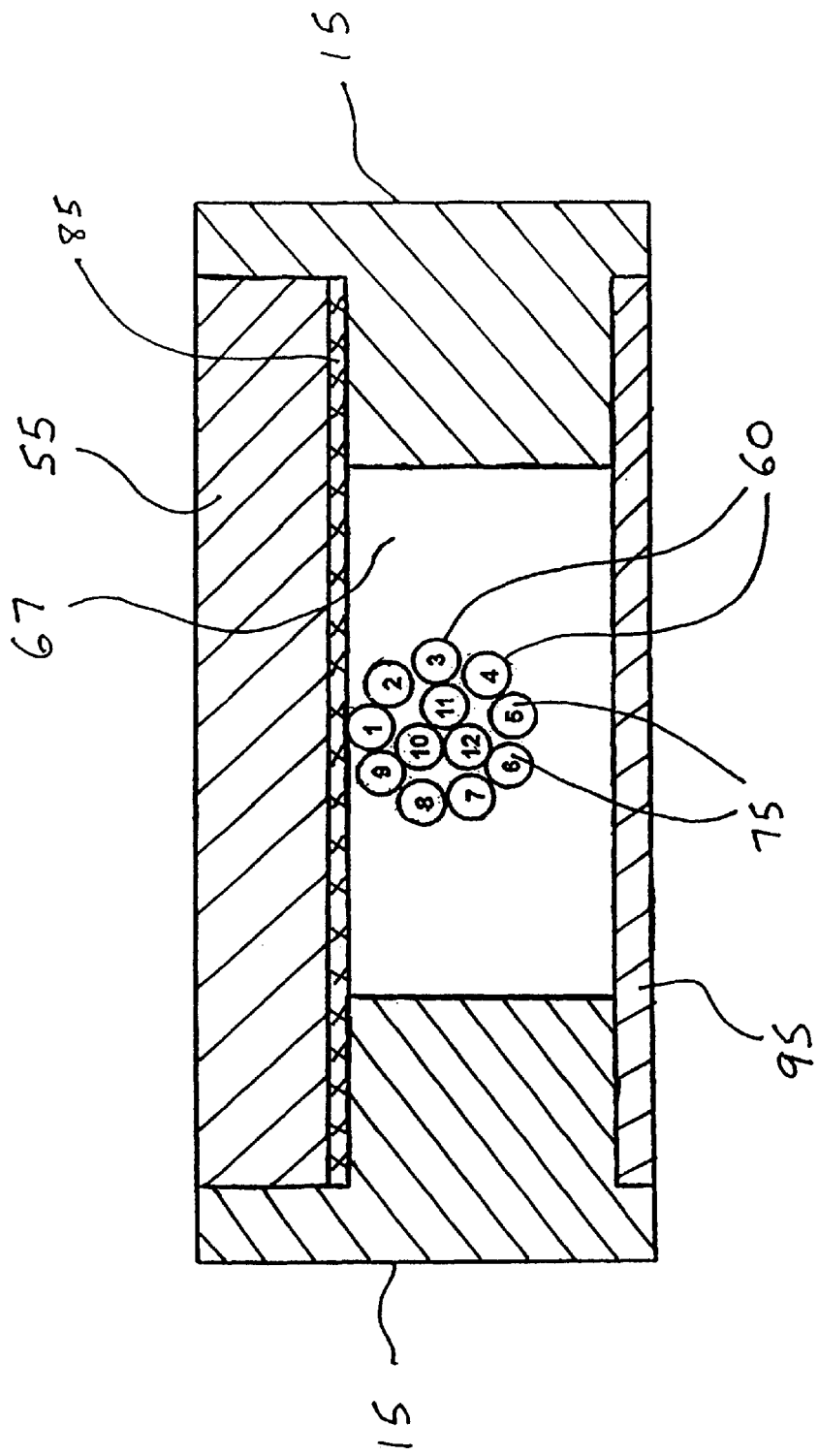
FIG. 3 is a cross-sectional view taken along line 3—3 of FIG. 2.
Figure 4:
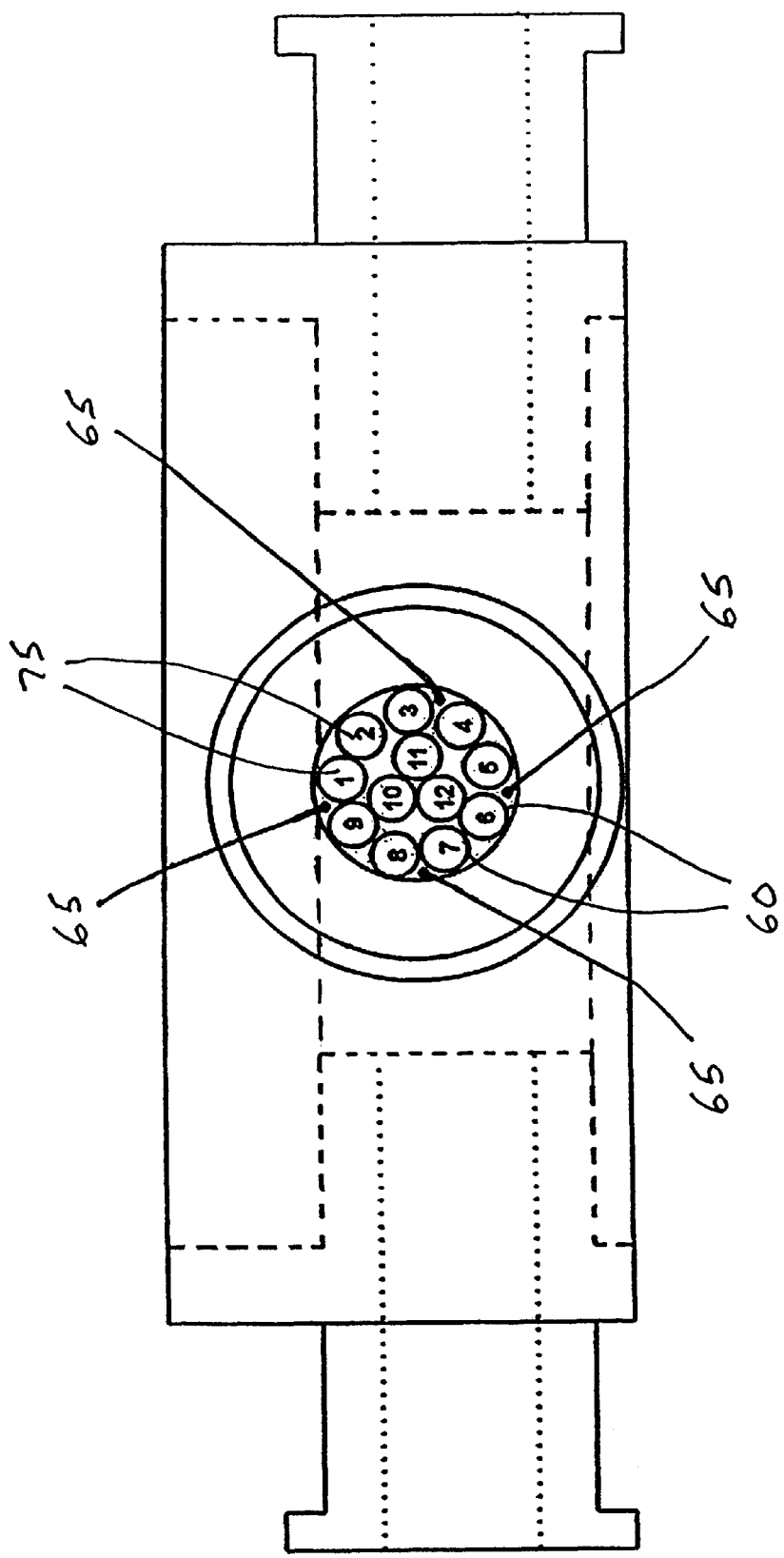
FIG. 4 is an end view of a cell and tissue culture modeling device 10 according to the present invention.
Figure 5:
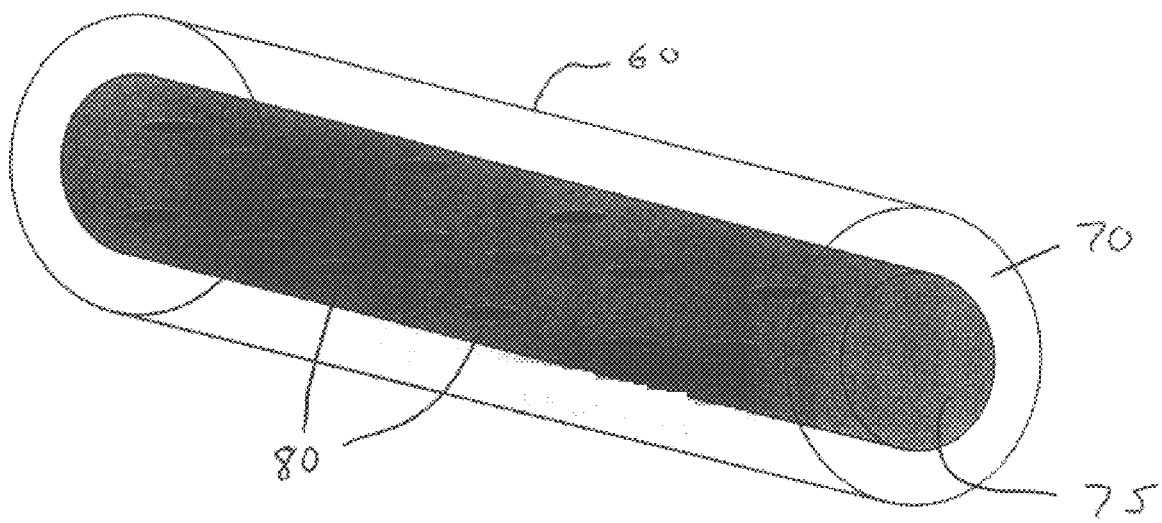
FIG. 5 is a perspective view of a hollow fiber 60 used in the present invention.

In FIGS. 3 and 4, the device 10 includes twelve hollow fibers 60 disposed within the interior chamber 57. The quantity of hollow fibers 60 can be limited to as few as one and can include more than twelve depending on the physical limitations of the housing 15, the inlet port 20, and the outlet port 25. The hollow fibers 60 traverse the length of the housing 15 between the inlet port 20 and the outlet port 25. Each of the hollow fibers 60 has a wall 70 and an interior defined as an intracapillary space 75. The hollow fibers 60 occupy only a portion of the internal chamber 57. The unoccupied portion of the internal chamber 57 is defined as an extracapillary space 67. The hollow fibers 60 can be bundled together in any suitable fashion (e.g., they can be placed adjacent to each other and secured together at the inlet port 20 and the outlet port 25 in a manner that permits fluid access into the intracapillary space 75. The hollow fibers 60 will generally be cut to the same order of length as the corresponding housing 15, and preferably slightly longer in order to accommodate the additional space of the inlet port 20 and outlet port 25. The exterior periphery of the bundled hollow fibers 60 is separated from the inner walls of the housing 15 at a distance sufficient to permit cell growth. The twelve hollow fibers 60 are suspended and secured in the inlet port 20 and the outlet port 25 using a medical grade epoxy adhesive 65. The epoxy adhesive 65 fixes the hollow fibers 60 in the inlet port 20 and outlet port 25 and seals the spaces in the inlet port 20 and outlet port 25 unoccupied by the hollow fibers 60. The epoxy adhesive 65 must create a watertight seal such that fluid entering the housing 15 through the inlet port 20 is only permitted to flow through the intracapillary spaces 75 of the hollow fibers 60 and not enter the extracapillary space 67. The hollow fibers 60 may be suspended and fixed using other suitable sealing means so long as the sealing means provides a durable, waterproof, and watertight seal yet retains the structural integrity of the housing 15. Examples of suitable sealing means include the use of an adhesive (e.g., a room temperature vulcanizing ("RTV")silicone glue) and various potting materials. However, the preferred epoxy adhesive 65 is obtained from Epoxy Technology and consists of two components that are mixed in the appropriate ratio prior to use. The epoxy adhesive 65 cures in two hours at 65° C. and exhibits shear strength of 1700 psi as well as an excellent optical profile.

In FIG. 4, hollow fibers 60 suitable for use in a device according to this invention are commercially available, and can be selected and positioned using known techniques, given the present description. Suitable hollow fibers 60 provide an optimal combination of such properties as gas permeability, strength, porosity, selectivity and biocompatability. Suitable hollow fibers include those commonly used for dialysis, ultrafiltration and/or microfiltration applications, e.g., having a molecular weight cut off from about 1 kD to about 1,000 kD. The hollow fibers 60 also include a plurality of pores 80 having a pore size from about 0.01 $\mu$m to about 5 $\mu$m. Particularly preferred are hollow fibers 60 having a pore size between about 0.01 $\mu$m and about 0.64 $\mu$m. The pores 80 that provide fluid communication between the intracapillary space 75 and the extracapillary space 67. Suitable hollow fibers can be constructed from a variety of materials, including polymers, graphite, ceramics (including porous glass fiber) and metals (e.g., stainless steel). Preferred are polymeric hollow fibers that provide an optimal combination of such properties as tensile strength, melt temperature, and glass transition temperature. Such hollow fibers can be formed, for instance, from cellulose (including regenerated cellulose and cellulose acetate), polyethylene, polypropylene, polysulfone, polymethyl methacrylate, polyacrylonitrile, poly(vinylidene fluoride) and the like. In the present invention, the hollow fibers 60 are made of polypropylene.

The polypropylene hollow fibers 60 each provide an inner diameter of between about 20 $\mu$m and about 1000 $\mu$m. Above this range, increasing inner diameters impose diffusional limitations on the cell mass, while below this range, decreasing inner diameters are more difficult to manufacture and to inoculate with cells. The preferred inner diameter for each hollow fiber 60 is between about 510 $\mu$m and about 690 $\mu$m. The hollow fibers 60 also each provide a wall thickness of between about 2 $\mu$m and about 200 $\mu$m. Below this range, fibers are typically not strong enough to withstand the steps involved in fabricating a device 10 according to the present invention, while above this range, hollow fibers 60 are too thick to allow adequate diffusion. The preferred wall thickness for each hollow fiber 60 is between about 155 μm and about 245 μm. The preferred outside diameter of the hollow fibers 60 is 1 mm.

Once secured in the housing 15, the twelve hollow fibers 60 are cut to a length of 8.6 cm. The functional length of each hollow fiber 60, that is, the length exposed to extracapillary influences, is 4.2 cm. The single hollow fiber 60 total volume (i.e., intracapillary space 75) is 0.024 mL giving a total intracapillary space 75 volume of 0.288 mL for all twelve hollow fibers 60. The calculated external surface area of a single hollow fiber 60 where the functional length is 4.2 cm is 0.079 $cm^2$ with a resultant surface area of 0.948 $cm^2$ for all twelve hollow fibers 60. The resultant volume is 0.095 $cm^2$ or 0.095 mL. The volume of the extracapillary space, which represents subtracting the exterior surface volume of the hollow fibers 60 from the volume of the interior chamber, is 3.433 mL (3.528–0.095). The ratio of extracapillary space 67 volume to intracapillary space 75 volume is approximately 35 (3.433/0.095), which is adequate for permeability determinations but also allows for multiple sampling of the internal chamber without emptying it completely. The cell culture models known in the art had a combined luminal surface area of approximately 75 $cm^2$ and thus the cell inoculation volume required is reduced by a factor of 3.85. The functional external surface area of a single hollow fiber 60 is 1.319 $cm^2$ which amounts to 15.828 $cm^2$ available for intraluminally-seeded cells.

Polypropylene hollow fibers 60 require rinsing with ethanol to reduce hydrophobic interactions prior to use as semipermeable membranes. Polypropylene in and of itself is a poor substrate for cellular attachment and thus requires application of a suitable matrix molecule prior to using it for successful cell culture. A fibronectin-like engineered protein polymer as well as the whole fibronectin molecule available from Sigma chemicals can be used for coating both the interior and exterior surfaces of the hollow fiber 60 prior to cell inoculation. Preferably, the hollow fibers 60 are lined with Pronectin™ from Polymer Technologies.

One important feature of the present invention is that a portion of the housing 15 is removable to access the extracapillary space 67. The shape and dimensions of that removable portion depends on the shape and dimensions of the housing. The removable portion can be attached utilizing any suitable attachment means known in the art including the use of threaded fasteners, hinge and latch combination, snap fit connection, etc. Because the hollow fibers 60 do not transmit light, no direct observation of the cells occupying the intracapillary space 75 is possible. However, with the ability to remove and replace a portion of the housing 15 without disrupting the experimental conditions, a hollow fiber 60 can be sterilely ligated and removed for sectioning and morphologic or immunocytochemical studies. Further, because of the accessibility of the extracapillary space 67 within the housing 15, introduction of tissue samples, neurochips, or other testing devices is possible.

The top wall 22 of the housing 15 includes a top panel 55 that may represent either a portion or all of the top wall 22. This top panel 55 is the removable portion of the housing that provides access to the extracapillary space 67. Preferably, the top panel 55 is a portion of the top wall 22 and is fashioned from polished acrylic. The top panel 55 may be fashioned from any suitable material so long as the material is capable of being sterilized (e.g., exposure to ethylene oxide) and is transparent in order to view the progress in the extracapillary space 67. The top panel 55 is attached to the housing 15 creating a watertight seal, yet is removable and resealable during the course of an experiment. The top panel 55 can be removably attached utilizing any suitable attachment means known in the art including other threaded fasteners, hinge and latch combination, snap fit connection, etc. The top panel 55 can utilize any sealing means known in the art including gaskets made from a variety of materials, RTV, tongue and groove connections, etc. Preferably, the attachment is accomplished by sealing the top panel 55 against the shelf 150 in the housing 15 with the use of a biologically inert USDA approved silicon gasket 85 and attaching the top panel 55 to the housing 15 using screws 90. Preferably, the shelf 150 that fits the top panel 55 is tapped for the appropriate screw size and fitted with stainless steel helicoil inserts 125 to prevent cracking of the polycarbonate housing 15.

The bottom wall 27 of the housing 15 may include a bottom panel 95 that may represent either a portion or the entire bottom wall 27. Preferably, the bottom panel 95 is a portion of the bottom wall 27 and is constructed using 1 mm thick laboratory quality glass. The bottom panel 95 is permanently attached to the bottom of the housing 15 using an epoxy adhesive 65 that creates a watertight seal between the bottom panel 95 and the housing 15. The preferred epoxy adhesive 65 is the same epoxy adhesive as identified above. Other suitable sealing means may be used so long as the sealing means provides a durable, waterproof, and watertight seal yet. Glass was chosen as the material for the bottom panel 95 in order to allow for inverted light microscopy observation as well as fluorescence imaging of cells in the extracapillary space 67. However, the bottom panel 95 may be constructed of any suitable material so long as the material is capable of being sterilized (e.g., exposure to ethylene oxide) and is transparent in order to view the progress in the extracapillary space 67. The distance from the low power objective to the bottom of the top panel 55 is within the resolution range of a standard inverted light microscope and cells occupying that compartment and their interactions with the hollow fibers 60 can be seen.

Once the hollow fibers 60 are secured in the housing 15, the entire unit is generally sterilized with ethylene oxide. Then the hollow fibers 60 are then flushed with ethanol, rinsed, and then coated with the sterile matrix preparation prior to use in experiments. If the completed units are to be stored prior to use, the hollow fibers 60 must remain wet during storage in order to prevent reformation of the hydrophobic interactions and loss of porosity.

Figure 6:
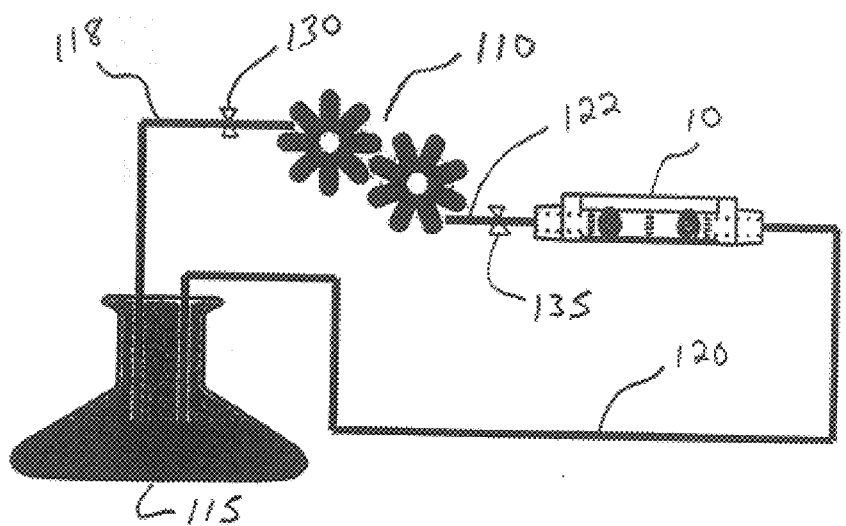
FIG. 6 is a schematic of a cell and tissue culture modeling apparatus 140 according to the present invention utilizing one cell and tissue culture modeling device 10.

In another embodiment, the present invention provides for a dynamic three-dimensional cell and tissue culture modeling apparatus (hereinafter referred to as "apparatus"). FIG. 6 depicts the apparatus 140 comprising one device 10 according to the present invention, a pump system 110, and a media reservoir 115. The media reservoir 115 is interconnected to the pump system by a first conduit 118. The pump system is interconnected to the inlet port 20 of each device by a second conduit 122. The outlet port 25 of each device is interconnected to the media reservoir 115 by a third conduit 120.

Preferably, the pump system 110 is a variable-speed pulsatile pump that generates flow from the media reservoir 115 through the hollow fibers 60 of the device 10 and back to the media reservoir 115. The variable-speed pulsatile pump comprises a central eccentric camshaft that extends and retracts four separate sets of stainless steel pins in a piston-like fashion. The pins are positioned to compress the flowpath in a rhythmical fashion to generate pulsatile flow. Through the use of different pin lengths and pump speed settings, the pumping mechanism is capable of generating flow levels of 1–50 mL/min with associated shear stress levels of 1–200 dyne/cm$^2$. Shear stress levels are estimated to be in the range of 1–5 dyne/cm$^2$ at the capillary level in vivo, but the pump system 110 allows for the study of endothelial cell responses to flow and associated investigations at even large artery levels of shear stress. Preferably, a first one-way valve 130 is positioned between the media reservoir 115 and the pump system 110 and a second one-way valve 135 is positioned between the pump system 110 and the device 10 to ensure unidirectional flow.

Figure 7:
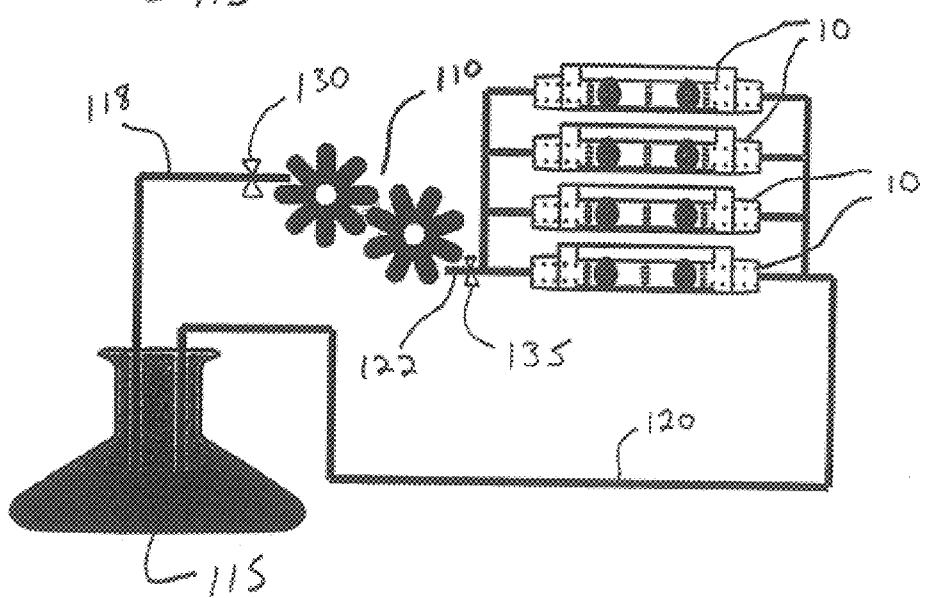
FIG. 7 is a schematic of a cell and tissue culture modeling apparatus 145 according to the present invention utilizing four cell and tissue culture modeling devices 10.

FIG. 7 shows a dynamic three-dimensional cell and tissue culture modeling apparatus 145 employing four devices 10 utilizing a singular pump system 110 and media reservoir 115. The modularity of the device 10 according to the present invention combined with the functionality of the current pump system 110 allows for four different flow settings on the same stage utilizing the same pump speed setting This feature is not available in cell culturing models known in the art. Under the current configuration, it is possible to envision four sets of different experimental flow conditions with up to eight replicates in each set, all within one laboratory incubator. The entire model when assembled has interlocking tabs and grooves that allow for complete modularity and employment of several models exposed to the same experimental conditions.

In the apparatus 140 including one device 10 and the apparatus 145 including four devices 10, the first conduit 118, second conduit 122, and third conduit 120 are constructed of a gas-permeable tubing in order to provide gaseous exchange for the cellular constituents of any culture system employed in this model. Such tubing can be formed of any suitable material that provides sufficient oxygen transport, but preferably the material is silicon.

The gas-permeable silicon tubing of sufficient length is used to connect the media reservoir 115 to the pump system 110, the pump system 110 to the inlet port 20 of the device 10, and the outlet port 25 of the device 10 to the media reservoir 115. All tubing connections are made with standard and readily available 5/16" connectors that allow for intercalation of sampling stopcocks, electrodes for transendothelial electrical resistance measurement, injection sites, etc. Although the preferred size of tubing is to fit 5/16" connectors, the optimal dimensions of the tubing, e.g., outer diameter, inner diameter, and in turn, wall thickness can be determined on a case by case basis, for instance, based on the intended use.

Once the device 10 is constructed, sterilized, and the hollow fibers 60 are coated with a suitable matrix material, the apparatus 140 is then ready for use in experiments. The device 10 is connected to a sterile flowpath and media reservoir 115 circuit and the media reservoir 115 is filled with an appropriate volume of growth media. The circuit is then pumped by hand until the entire tubing volume and intervening device 10 is filled. The extracapillary space 67 is filled with growth media as well. The apparatus is then "primed" for 24–72 hours with complete growth media in an incubator. This enables any air bubbles that form on media warming to be evacuated as well as impregnates the interstices of the hollow fibers 60 with growth factors and nutrients present in the media. After adequate priming, the device 10 is ready for inoculation of cells into the intracapillary spaces 75 of the hollow fibers 60. Under sterile conditions, the device 10 is removed from the flowpath and an appropriate suspension of cells is prepared in approximately 3 mL of media. The cell suspension is then flushed back and forth gently through the intracapillary spaces 75 of the hollow fibers 60 with syringes to promote even distribution. Care is taken not to introduce any air into the intracapillary spaces 75 of the hollow fibers 60 that might prevent cellular attachment. The remaining media in the syringes is then filtered through the hollow fibers 60 into the extracapillary space 67 and the unit is incubated for 1–3 hours without flow while the cells attach. During this period, the unit is rotated 180 degrees every 45 minutes to promote circumferential distribution of the cell suspension in the intracapillary spaces 75. The unit is then reconnected to the flowpath and flow is initiated at a very low rate. After an initial adaptation period, flow can be increased as needed to meet the metabolic requirements of the cells employed or to generate the desired experimental conditions. At any point in time after the cell suspension in the intracapillary spaces 75 have adapted to the presence of flow, a second cell suspension may be added to the extracapillary space 67. The procedure is similar to loading of the intracapillary spaces 75 of the hollow fibers 60, except that the flow may be continued throughout the process. The model conditions are thus established and monitoring for the culturing of the cell suspensions can then commence. The entire apparatus, when primed with cell culture media at 37° C., does not leak and allows for hands-on access to the extracapillary space 67 during the conduction of an experiment.

Figure 8:
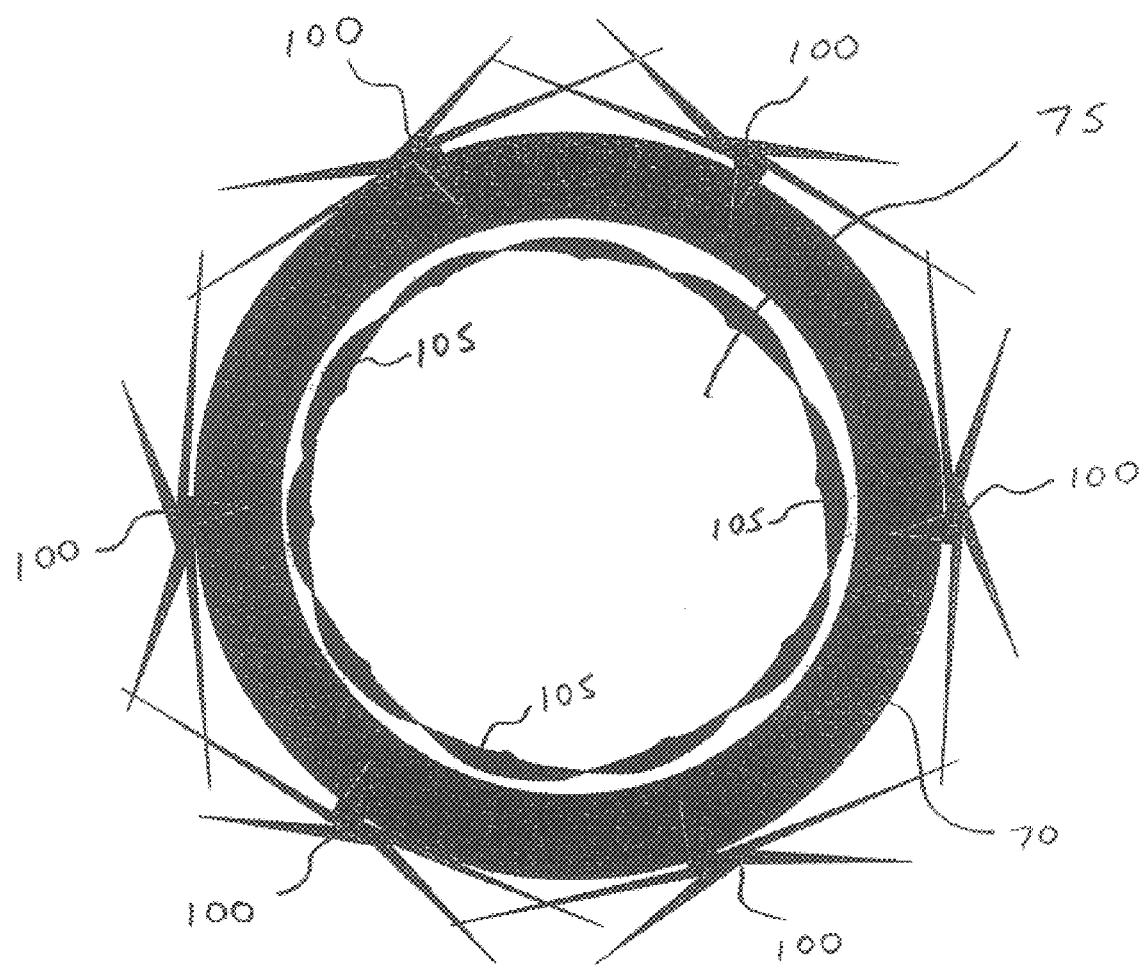
FIG. 8 is a cross-sectional view of a hollow fiber 60 after inoculation of the intracapillary space 75 with endothelial cells 105 and inoculation of the extracapillary space 67 with astrocytes 100.
Figure 9:
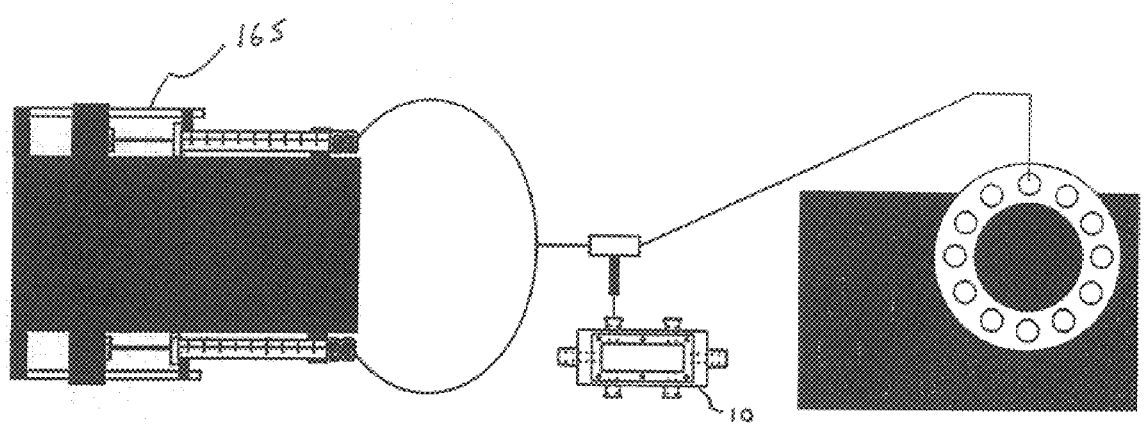
FIG. 9 is a schematic of a microdialysis-driven robotically assisted sample collection system used in conjunction with a cell and tissue culture modeling device 10 according to the present invention.

As shown in FIG. 8, to simulate the blood brain barrier in vitro utilizing the present invention, each intracapillary space 75 of each hollow fiber is preferably inoculated with primary cultures of rodent brain microvascular endothelial cells 105 and the extracapillary space 67 is preferably inoculated with primary cultures of rodent whole brain astrocytes 100. As a blood brain barrier model, the apparatus according to the present invention can be utilized in many different ways such as drug permeability tests, drug efficacy tests, electrophysiology studies, and gene expression studies. Because the present invention can successfully provide a biological model the blood brain barrier when the intracapillary spaces are inoculated with endothelial cells and the extracapillary space is inoculated with glial cells, drug permeability tests may be performed to estimate the permeability of a novel pharmaceutical agent into the central nervous system. To accomplish this test, a known concentration of a drug is dissolved directly into the media reservoir. The drug is then directed from the media reservoir through the plurality of intracapillary spaces in the device. Samples can then be taken from the extracapillary space via the access port in the device. Sampling can be conducted manually or can be automated through the use of a robotically assisted sample collection device such as a microdialysis driven sample collection device 165 as shown in FIG. 9. The samples are then analyzed to determine the permeability of the drug from the plurality of intracapillary spaces to the extracapillary space.

To conduct a permeability study, a known concentration of a drug under investigation is dissolved directly into the media reservoir and perfused through the intracapillary spaces. Samples were taken from the extracapillary space and analyzed. The analysis of the samples was performed by HPLC (theophylline and 8-STP) or by detection of radioactive tracers.

Because the sampling can be automated, time course profiles of entry or exit of a substance from the intracapillary space or extracapillary space can be accomplished with very little user intervention subsequent to initializing the protocol. This drastically reduces the possibility of error or contamination of experiments in progress and ensures the validity of the results obtained. Precise control over sample volumes and replacement compositions is very advantageous. The flexibility of such a system or device permits opportunities in fields of drug-delivery, cancer chemotherapy, epilepsy research, and CNS metabolism. Extrapolation to other tissue and organ specificities can be easily accomplished and valuable information can be obtained in areas such as inflammation and wound healing, renal and hepatic function, and hematopoiesis.

In general, the efficacy of chemotherapeutic agents in the postoperative treatment of a primary central nervous system malignant tumor is very poor with a high degree of undesirable side effects. In many cases, a functional blood-brain barrier is implicated in the failure of these agents to successfully reach and treat the malignancy, rather than a conclusion that the tumor exhibits an inherent resistance to the agent. In the present invention, a tissue sample from an operative tumor resection can be introduced into the extracapillary space in a device already exhibiting the characteristics of a functional blood brain barrier. Various chemotherapeutic agents can then be passed through the intracapillary spaces and the tumor response monitored through metabolic parameters. Additionally, administering the agent to the extracapillary space can directly assess the response of the tumor to the agent in question. If the tumor responds to the agent under direct exposure, then passing the agent through the intracapillary spaces in the model will determine the ability of the agent to penetrate the blood brain barrier. If the tumor responds to the agent, then the agent has successfully penetrated the blood brain barrier. If the tumor fails to respond, then a conclusion can be made that the agent did not penetrate the blood brain barrier. In this way, drug resistance can be more definitively demonstrated or disproven, and other adjutant therapies can be considered if necessary.

Figure 10:
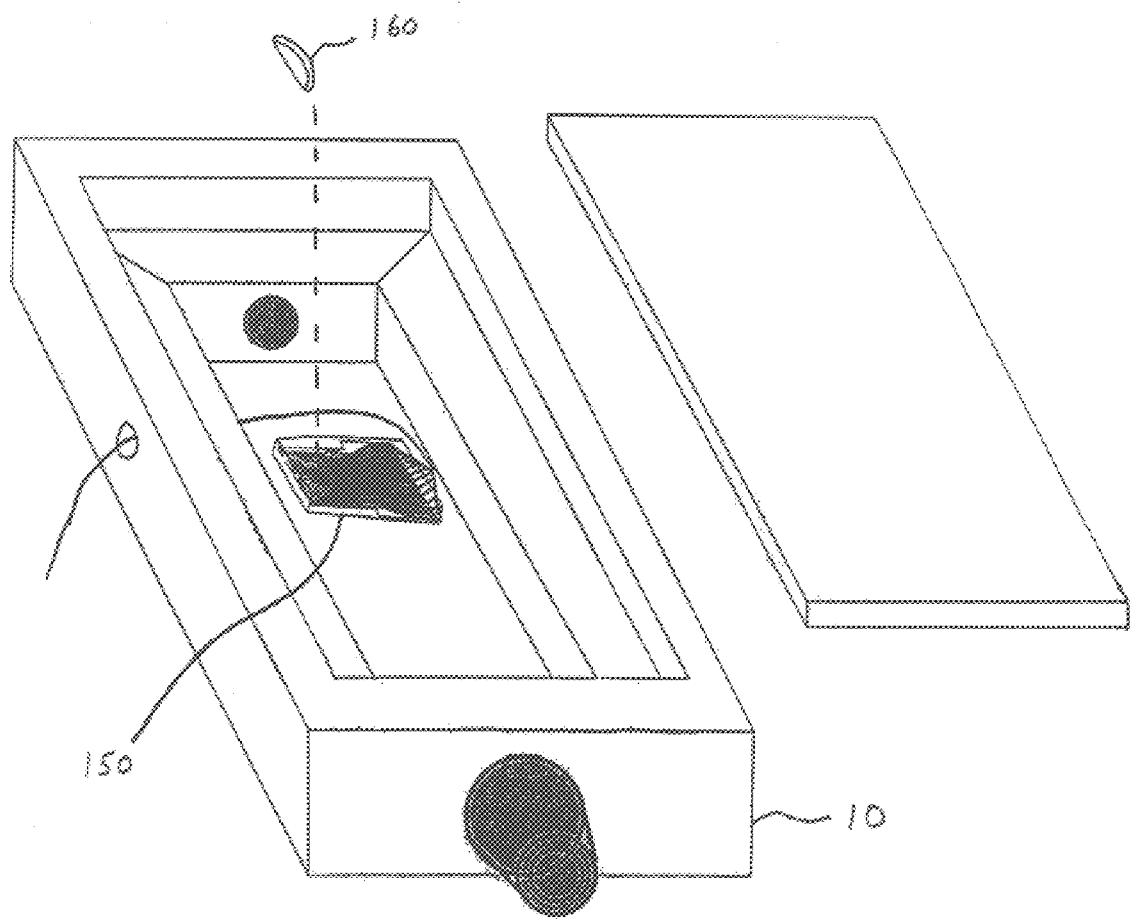
FIG. 10 is a perspective view of a cell and tissue culture modeling device 10 according to the present invention utilizing a neurochip 150 and a brain tissue sample 160 to determine drug efficacy.
Figure 11:
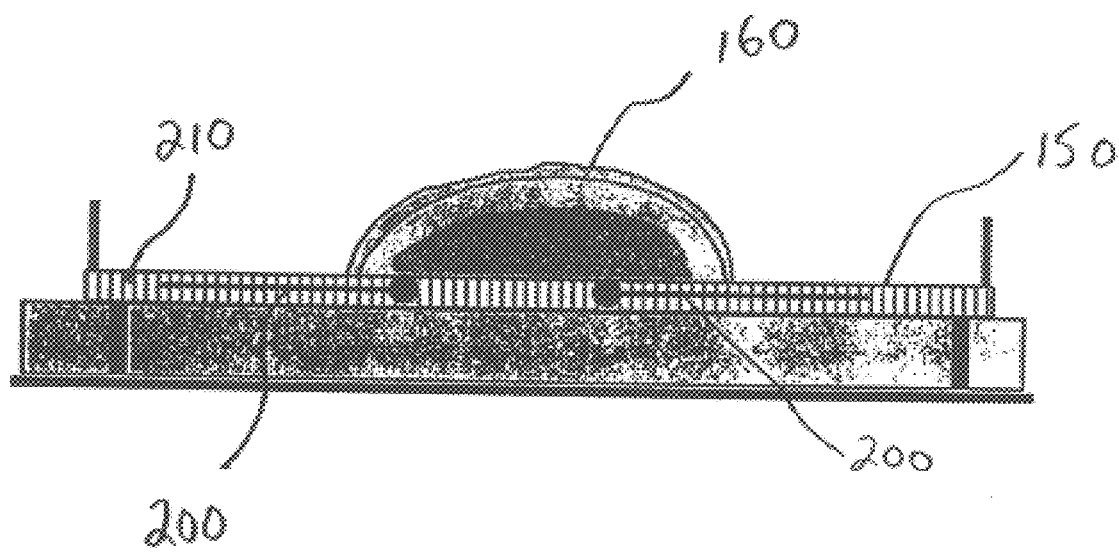
FIG. 11 is a side view of a brain tissue sample 160 placed onto a neurochip 150.

A corollary to this proposed experimental design is the implantation of a neurochip (e.g., micro-electrode array) and a brain tissue sample into the extracapillary space of a device already exhibiting the characteristics of a functional blood brain barrier to study the electrophysiology activity of the brain tissue sample. According to the present invention, as shown in FIGS. 10 and 11, the neurochip 150 is first introduced into the extracapillary space of the device 10 and then the brain tissue sample 160 is placed onto the neurochip 150. An example of the preparation of the brain tissue sample for testing is described in "An in vitro blood-brain barrier model: Cocultures between endothelial cells and organotypic brain slice cultures", Duport, S., Neurobiology, Vol. 95, February 1998, which is hereby incorporated by reference in its entirety. A neurochip 150 is a device for monitoring and recording the electrophysiological phenomena in excitable tissular explants or organotypic tissue cultures. A typical neurochip 150 includes a plurality of electrodes 200 embedded in a permeable membrane 210. The electrodes 200 can record signals emitted from the brain tissue sample and/or deliver electrical impulses to stimulate the brain tissue sample. All the electronic aspects of the neurochip may be driven by a PC via an AD/DA board. An example of a neurochip is utilized and described in U.S. Pat. No. 5,759,846 to Stoppini et al., which is hereby incorporated by reference in its entirety. U.S. Pat. No. 5,759,846 to Stoppini et al. describes a device that is capable of keeping an explanted or cultured tissue sample alive and allowing the electrophysiological and biochemical activity of the tissue sample studied to be continuously measured and analyzed. In a preferred embodiment, the brain tissue sample is an epileptic brain tissue sample and the device 10 is used to conduct electrophysiology studies for assessment of the efficacy of anticonvulsant agents. Spontaneously firing epileptic brain tissue samples can be subjected to different anticonvulsant agents and the response to the agents can be determined. Since those patients referred for operative resection as a treatment for epilepsy are already felt to be drug resistant, much can be learned from the response of this epileptic brain tissue to anticonvulsant agents in vitro, with and without an intervening blood-brain barrier. Combined with the use of various receptor agonists and antagonists, a great deal of knowledge stands to be obtained from studies of this nature.

Furthermore, the present invention provides the capability of conducting gene expression studies. The user has the ability to expose and remove single or multiple fibers during the course of an experiment that offers a tremendous advantage over single use models. For example, a detailed time course of endothelial cell changes in response to a particular stimulus may be observed. This advantage is particularly evident when taken into consideration with state of the art DNA microarrays currently available. In a typical experiment, endothelial cells are seeded in the model and exposed to a particular stimulus. A capillary is then removed at predetermined time points for analysis and the experimental conditions are continued. Cellular RNA, DNA, metabolites, or protein is then removed from the capillary and converted/amplified to a cDNA that can then be subjected to hybridization with a number of available gene filters. The ability to track changes in gene expression across multiple early time points over the course of a single experiment is unprecedented in modern science.

Finally, the genesis of the blood-brain barrier is currently an area of intense interest in CNS physiology. As was described in the introduction, it is believed that astrocytes secrete one or more "permissive" or "inducing" factors that promote differentiation and maturation of cerebrovascular endothelial cells. To date, however, little is known regarding the identity of this factor(s) and the mechanism by which endothelial cells in the capillaries of the brain respond to it. Moreover, it is also not known whether the endothelial cells themselves secrete a factor which astrocytes may recognize and in response, initiate the induction process. Given the failure of astrocyte-conditioned media to induce a barrier phenotype in dedifferentiated endothelial cells, this is a distinct possibility. The proposed model offers a unique way to approach the study of this situation. Given the small size and modularity of the system, a circuit between the extracapillary compartments of a model with an established barrier and a model with endothelial cells only can be created. By establishing chemical equilibrium between the two respective compartments, one can determine if the endothelial cells seeded alone develop a barrier phenotype. If this occurs, the protein content of the "inducing" media can then be compared to "plain" media and prospective candidates for the permissive factor(s) can be identified through two-dimensional protein electrophoresis.

Aside from the study of the blood-brain barrier, the model can be utilized to study the physiology of cells (e.g. endothelial) from a variety of sources and their attendant responses to flow and extraluminal influences. We have used endothelial cells from human cerebral aneurysm specimens in the model to try and illuminate the gene expression changes that occur in the genesis of aneurismal arterial dilatations. Other cell types besides endothelial cells may be employed in the model as well. For example, in collaboration with other investigators, canine renal epithelial cells have been seeded in the model in an attempt to track the phenotypic changes in response to simulated urine flow. A further modification of this experimental design will be to actually subject the extraluminal compartment to flow as opposed to the luminal compartment. This protocol may better mimic the conditions which exist in vivo as it is the basolateral membrane of these particular cells which is exposed to the flow of nutrients and oxygen as opposed to the apical membrane which lines the renal tubular system.

A number of other experimental paradigms may also be possible utilizing the capabilities of the currently proposed model. Experimental reconstructions of the biliary canalicular system using cocultured hepatocytes and biliary epithelial cells as well as further modifications of the renal glomerular model are only a few brief examples.

While this invention has been described with an emphasis upon a preferred embodiment, it will be obvious to those of ordinary skill in the art that variations of the preferred embodiment may be used and that it is intended that the invention may be practiced otherwise than as specifically described herein.

What is claimed is:

1. A cell and tissue culture modeling device comprising:
   a housing having an interior chamber, wherein said housing includes a top wall and a bottom wall, said top and bottom walls are flat and parallel;
   an inlet port in fluid communication with said internal chamber;
   an outlet port in fluid communication with said internal chamber,
   a plurality of hollow fibers disposed within said interior chamber and traversing the length of said housing between said inlet port and said outlet port, each of said plurality of hollow fibers has an interior defining an intracapillary space;
   said interior chamber defines an extracapillary space unoccupied by said plurality of hollow fibers;
   wherein at least a portion of said housing is removable to access said extracapillary space;
   wherein said housing includes a pair of opposing end walls and a pair of opposing side walls, at least one of said pair of opposing side walls includes at least one access port in fluid communication with said extracanillary space; and said extracapillary space being suitable for observation on a mircroscope.

2. The device of claim 1, wherein each of said plurality of hollow fibers has a wall that includes a plurality of pores that provide fluid communication between said intracapillary space and said extracapillary space.

3. The device of claim 2, wherein said plurality of hollow fibers are formed of a material selected from the group consisting of polypropylene, polyester, polystyrene, polycarbonate, nitrocellulose compound, polyethylene, polysolfone, cellulose, polymethyl methacrylate, polyacrylonitrile, and polyvinylidene fluoride.

4. The device of claim 1, wherein said inlet port is located in one of said pair of opposing end walls and said outlet port is located in the other of said pair of opposing end walls.

5. The device of claim 4, wherein said plurality of hollow fibers are suspended and fixed in said inlet port and outlet port using an epoxy adhesive to create a watertight extracapillary space.

6. The device of claim 1, further comprising a neurochip installed in said extracapillary space.

7. A cell and tissue culture modeling device comprising:
   a housing having an interior chamber;
   an inlet port in fluid communication with said internal chamber;
   an outlet port in fluid communication with said internal chamber;
   plurality of hollow fibers disposed within said interior chamber and traversing the length of said housing between said inlet port and said outlet port, each of said plurality of hollow fibers has an interior defining an intracapillary space;
   said interior chamber defines an extracapillary space unoccupied by said plurality of hollow fibers;
   wherein at least a portion of said housing is removable to access said extracapillary space;
   wherein said housing includes a top wall and a bottom wall, said top and bottom walls are flat and parallel;
   wherein at least a portion of said bottom wall defines a bottom panel; and said bottom panel is made of laboratory quality glass.

8. A cell and tissue culture modeling device comprising:
   a housing having an interior chamber;
   an inlet port in fluid communication with said internal chamber;
   an outlet port in fluid communication with said internal chamber;
   a plurality of hollow fibers disposed within said interior chamber and traversing the length of said housing between said inlet port and said outlet port, each of said plurality of hollow fibers has an interior defining an intracapillary space;
   said interior chamber defines an extracapillary space unoccupied by said plurality of hollow fibers;
   wherein at least a portion of said housing is removable to access said extracapillary space;
   wherein said housing includes a top wall and a bottom wall, said top and bottom walls are flat and parallel;
   wherein at least a portion of said top wall defines a top panel; and the top panel is removably attached to said housing and includes a gasket installed in between said top panel and said housing to create a watertight seal of said extracapillary space;
   wherein said top panel is the portion of said housing that is removable to access said extracapillary space; and
   wherein said top panel is made of polished acrylic.

9. A method of determining the permeability of an agent across a capillary wall comprising the steps of:
   providing a cell culture model having a plurality of capillaries disposed within an interior chamber which defines an extracapillary space unoccupied by said plurality of capillaries, each of said plurality of capillaries including a plurality of pores that provide fluid communication between an intracapillary space and said extracapillary space;
   passing an agent having a known concentration through said plurality of intracapillary spaces;
   sampling said extracapillary space to provide an extracapillary space sample;
   visualizing said cell culture in said extracapillary space under a microscope; and
   analyzing said extracapillary space sample to determine the permeability of said agent across each of said capillary walls.

10. The method of claim 9, wherein said plurality of intracapillary spaces are inoculated with endothelial cells.

11. The method of claim 9, wherein said extracapillary space is inoculated with glial cells.

12. The method of claim 9, wherein said sampling step is accomplished by a microdialysis-driven sample probe.

13. The method of claim 12, further comprising a second cell culture modeling device to allow for the simultaneous determination of permeability values of at least two agents in a single experiment.

14. A method of determining the efficacy of a drug comprising the steps of:
   providing a model that exhibits the properties of a functional blood brain barrier, said model having a plurality of intracapillary spaces and an extracapillary space accessible by an access panel;
   removing the access panel;
   placing a tissue sample into said extracapillary space;
   passing an agent through said plurality of intracapillary spaces;
   analyzing said tissue sample for responsiveness to said agent; and
   replacing the access panel and continuing the said drug efficacy determination.

15. The method of claim 14, wherein said tissue sample is a brain tissue sample.

16. The method of claim 15, wherein said agent is a chemotherapeutic agent.

17. The method of claim 14, wherein said tissue sample is a brain tissue sample.

18. The method of claim 17, further comprising the step of placing a neurochip in said extracapillary space before placing said brain tissue sample into said extracapillary space, said neurochip is capable of studying the electrophysiological activity of said brain tissue sample.

19. The method of claim 18, wherein said brain tissue sample is placed onto the surface of said neurochip.

20. The method of claim 19, wherein said brain tissue sample is an epileptic brain tissue sample.

21. The method of claim 20, wherein said agent is an anticonvulsant agent.

22. The method of claim 14, further comprising the step of examining said tissue sample in said extracapillary space with a microscope.

23. A method of determining gene expression over time in cells comprising the steps of:
   providing a cell culture model having a plurality of hollow fibers disposed within an interior chamber which defines an extracapillary space unoccupied by said plurality of hollow fibers, each of said plurality of hollow fibers includes an intracapillary space inoculated with a cell suspension;
   removing the access panel;
   passing an agent through said plurality of intracapillary spaces;
   sampling at least one of said plurality of intracapillary spaces by removing at least one of said plurality of hollow fibers over time;
   removing cellular material from at least one of said plurality of hollow fibers;
   analyzing the gene expression of said cellular material; and
   replacing the access panel and continuing the gene expression determination in said cells.

24. The method of claim 23, wherein said cellular material is selected from the group consisting of RNA, DNA, metabolites, and protein.

25. A method of determining the efficacy of a drug comprising the steps of:
   providing a model that exhibits the properties of a functional blood brain barrier, said model having a plurality of intracapillary spaces and an extracapillary space accessible by an access panel;
   placing a tissue sample into said extracapillary space;
   passing an agent through said plurality of intracapillary spaces;
   visualizing said tissue in said extracapillary space under a microscope; and
   analyzing said tissue sample for responsiveness to said agent.

26. The method of claim 25, wherein said tissue sample is a cancerous tissue sample.

27. The method of claim 25, wherein sad agent is a chemotherapeutic agent.

28. The method of claim 25, wherein said tissue sample is a brain tissue sample.

29. The method of claim 28, further comprising the step of placing a neurochip in said extracapillary space before placing said brain tissue sample into said extracapillary space, said neurochip is capable of studying the eleotrophysiological activity of said brain tissue sample.

30. The method of claim 29, wherein said brain tissue sample is placed onto the surface of said neurochip.

31. The method of claim 30, wherein said brain tissue sample is an epileptic brain tissue sample.

32. A method of determining gene expression over time in cells comprising the steps of:
   providing a cell culture model having a plurality of hollow fibers disposed within an interior chamber which defines an extracapillary space unoccupied by said plurality of hollow fibers, each of said plurality of hollow fibers includes an intracapillary space inoculated with a cell suspension;
   passing an agent through said plurality of intracapillary spaces;
   sampling at least one of said plurality of intracapillary spaces by removing at least one of said plurality of hollow fibers over time;
   removing cellular material from at least one of said plurality of hollow fibers;
   visualizing said cells in said extracapillary space under a microscope; and
   analyzing the gene expression of said cellular material.

33. A method of determining the permeability of an agent across a capillary wall comprising the steps of:
   providing a cell culture model having a plurality of capillaries disposed within an interior chamber which defines an extracapillary space unoccupied by said plurality of capillaries, each of said plurality of capillaries including a plurality of pores that provide fluid communication between an intracapillary space and said extracapillary space;
   removing the access panel;
   passing an agent having a known concentration through said plurality of intracapillary spaces;
   sampling said extracapillary space to provide an extracapillary space sample;
   analyzing said extracapillary space sample to determine the permeability of said agent across each of said capillary walls; and
   replacing the access panel and continuing the determination of the permeability of said agent across each of said capillary walls.

* * * * *